United States Patent
Hunter

(10) Patent No.: US 8,292,796 B2
(45) Date of Patent: Oct. 23, 2012

(54) MAGNETIC APPARATUS TO TREAT PAIN IN ANIMALS

(75) Inventor: Clifford Wayne Hunter, Luling, TX (US)

(73) Assignee: Cielo Trust, Luling, TX (US)

( * ) Notice: Subject to any disclaimer, the term of this patent is extended or adjusted under 35 U.S.C. 154(b) by 440 days.

(21) Appl. No.: 12/545,593

(22) Filed: Aug. 21, 2009

(65) Prior Publication Data

US 2010/0056845 A1    Mar. 4, 2010

Related U.S. Application Data

(60) Provisional application No. 61/092,097, filed on Aug. 27, 2008.

(51) Int. Cl.
*A61B 17/52* (2006.01)
*A61N 2/00* (2006.01)

(52) U.S. Cl. .............................................. 600/9; 600/15
(58) Field of Classification Search .................. 600/9, 15
See application file for complete search history.

(56) References Cited

U.S. PATENT DOCUMENTS

| | | | | |
|---|---|---|---|---|
| 4,587,956 A | * | 5/1986 | Griffin et al. ................... | 600/15 |
| 5,752,911 A | * | 5/1998 | Canedo et al. ................... | 600/9 |
| 6,819,210 B2 | * | 11/2004 | Boynton et al. ............... | 335/299 |
| 2004/0181116 A1 | * | 9/2004 | Kent et al. .......................... | 600/9 |
| 2006/0241333 A1 | * | 10/2006 | Hunter ............................. | 600/13 |
| 2007/0083237 A1 | * | 4/2007 | Teruel ................................ | 607/1 |
| 2007/0260291 A1 | * | 11/2007 | Hunter et al. ................... | 607/50 |
| 2008/0025552 A1 | * | 1/2008 | Dohi et al. ...................... | 381/421 |
| 2008/0246573 A1 | * | 10/2008 | Souder et al. ................. | 335/306 |

* cited by examiner

*Primary Examiner* — Charles A Marmor, II
*Assistant Examiner* — Sunita Reddy
(74) *Attorney, Agent, or Firm* — Buskop Law Group, PC; Wendy Buskop

(57) ABSTRACT

An apparatus for the treatment of chronic pain, through the use of an electro-magnetic field generated by the device. The apparatus comprises a frame with a continuous side wall and a central passageway extending there through with a bar disposed in the central passageway. The bar extends from one side of the continuous side wall the other side. Four pairs of identical planar pole magnets are embedded in the frame, and wherein each pair comprises two magnets which can have a planar face disposed adjacent the other and separated by less than 1 inch. A central magnet encircles the bar and can be disposed at the intersection of the donut-shaped low gauss magnet field wherein a central magnet is used for forming a substantially focused magnetic field.

12 Claims, 4 Drawing Sheets

MAGNETIC APPARATUS TO TREAT PAIN IN ANIMALS

CROSS REFERENCE TO RELATED APPLICATIONS

The present application claims priority and benefit of U.S. Provisional Application Ser. No. 61/092,097 filed on Aug. 27, 2008, entitled "Magnetic Apparatus to Treat Pain in Animals". This reference is hereby incorporated in its entirety.

FIELD

The present embodiments generally relate to a device used in therapy and/or for the relief of pain. The embodiments further relate to a device capable of producing a finite or substantially contained magnetic field or flux field. The device uses an intersecting magnetic flux fields for the treatment of chronic pain associated with various maladies, through the use of an electro-magnetic field generated by the device.

BACKGROUND

A need exists for a lightweight inexpensive device capable of relieving pain in animals, such as humans.

A further need exists for a device that can be modified to produce different strengths of magnetism for simultaneous treatment to four limbs of an animal.

The present embodiments meet these needs.

BRIEF DESCRIPTION OF THE DRAWINGS

The detailed description will be better understood in conjunction with the accompanying drawings as follows.

Figure 1A:
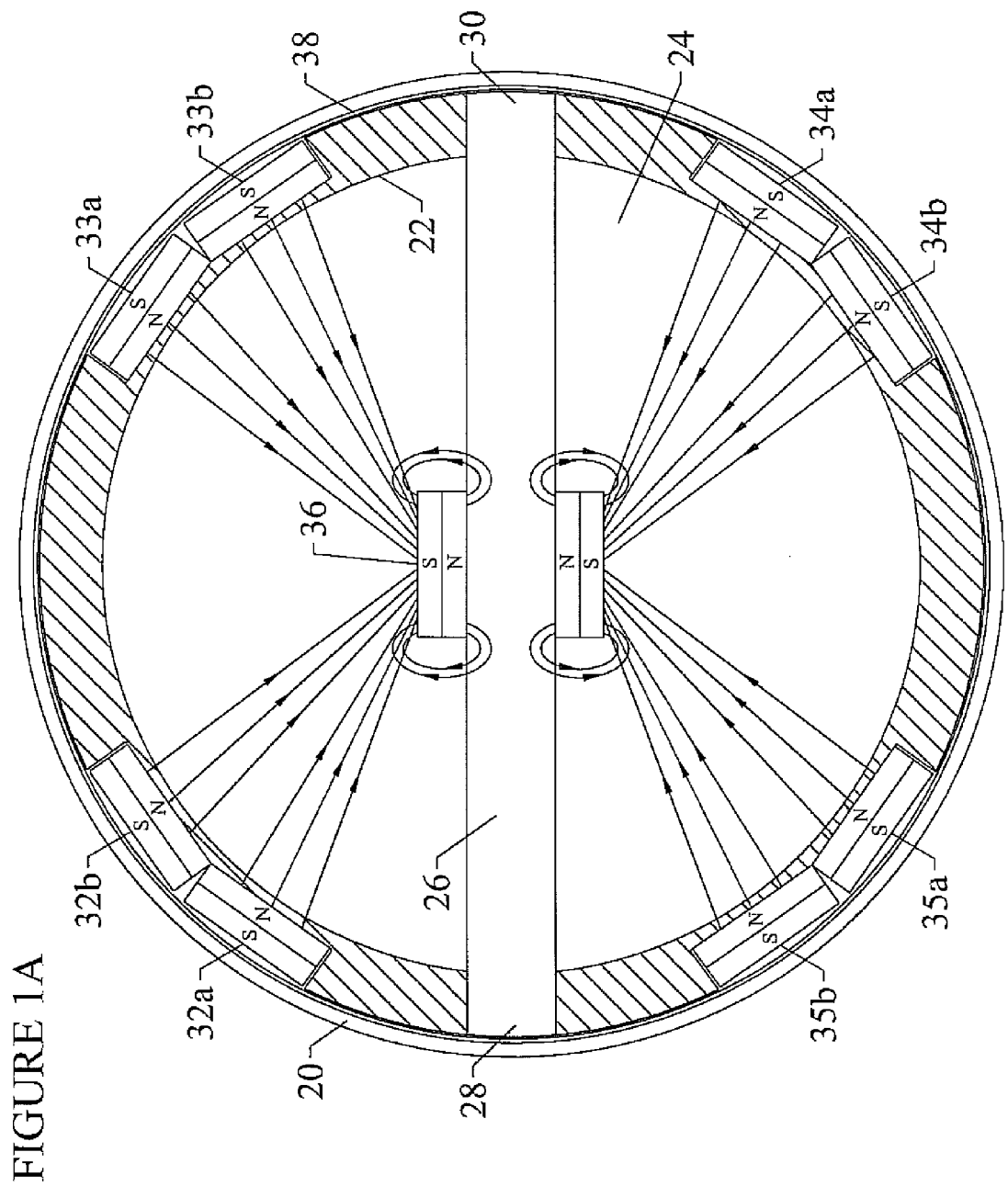
FIG. 1A is a cross-sectional view of an embodiment of the present invention showing the relative orientation of the magnets in the sidewall of the frame.

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways.

Magnetism indicates that each individual atom of magnetic substance is, in effect, a tiny magnet with a north pole and a south pole.

Magnetic properties of materials can be classified as diamagnetic, paramagnetic, and ferromagnetic. Their classification relates to the manner in which materials react in a magnetic field. The term, ferromagnetic, refers to a solid with a large susceptibility to a magnetic field, which exhibits spontaneous magnetism. Iron and steel are examples of solids which are strongly attracted to magnets, from which the term, ferromagnetic, is derived.

A magnetic field of flux can induce current flow in circuits. It can be contemplated that the magnetic fields of the present invention induce a very low current flow in the ferromagnetic properties of blood.

An embodiment of the present invention is directed to a device for establishing or otherwise creating a substantially contained finite, pair of donut-shaped magnetic fields that intersect with a planar magnetic field using magnets with planar faces.

An embodiment of the present invention can generate a magnetic field to relieve the symptoms associated with degenerative diseases and disorders including: pain, swelling, stiffness, etc. Humans or animals place an arm or leg in a portal that places them into proximity with the magnetic field.

The embodiments can be configured to include permanent magnets to create magnetism. A magnetic field produced by a permanent magnet source can constitute a first phase. The invention relates to multiple magnetic fields of the first phase variety and a second magnetic field that can be further described as opposing the first phase. An opposing field refers to a situation where the field lines of magnetic flow travel in opposing directions when two magnets face each other.

An additional embodiment can include permanent magnet pairs for producing a magnetic field where the field lines of the magnetic flux rotate clockwise or counterclockwise around a center, forming a donut shape when viewed from a hypothetical common cross-sectional face, and intersecting with a substantially planar magnetic field.

The embodiments can help relieve pain associated with degenerative diseases and disorders including wrist and hand pain by establishing a contained magnetic field and exposing the painful region to the field. An embodiment can include a plurality of permanent magnets oriented in a side by side axis parallel orientation such that the longitudinal axis and poles of a first magnet are placed adjacent to and parallel with the longitudinal axis of an adjacent or second magnet of similar polarity. The second magnet does not have to have identical configuration.

Symptomatic relief (e.g., lessening of pain or swelling, etc.) through the use of the present apparatus can occur within a central passage way consisting of a frame supporting with oriented embedded magnetic pairs that rest on a bar with a magnet that generates a planar field. A magnetic field emanating from the front or rear face (i.e., the spaced apart sides of the frame) can also be effective in focusing the magnetic field when a human, or an animal, has a limb resting on the central bar.

The frame can be shaped to form a circle in cross section, which can have a generally cylindrical shape. It can be contemplated that the frame can be rectangular, square or another shape which has continuous side walls.

The frame can have a central passageway or opening. An enclosed shape establishes the desired confined or finite intersecting fields.

A circular magnet disposed around a bar that stretches from one internal side to another internal side of the frame creates a contained, finite, or planar magnetic field.

In an embodiments the central magnet acts as a focus for the magnetic fields generated by the surrounding magnets. This magnetic focus is used for therapeutic relief of pain and swelling. Cells, such at blood cells, can exhibit magnetic properties and can be thought of as having poles and a zero. As these cells pass through a magnetic field in various orientations, the cells can become charged in such a way that promotes cell separation. Cell separation helps improve circulation, which can both reduce swelling and relieve symptomatic pain.

It is important to point out that the terms "finite", "planar", and "contained" are used in a relative sense. The magnetic field established within the area bounded by the frame (i.e., the passageway) has a magnetic field which can vary in flux density depending upon the location sampled, but the field shall remain confined, finite, and have the shape of intersecting donuts with respect to the physical boundary of the frame. This defines the size and shape of the treatment passageway.

As the shape of the magnetic field changes, it is important that the pairs of magnets remain embedded in the side wall and not be removable because a gap can be created in the field.

A liner can be used over the frame to insulate the magnetic field, and concentrate the field towards the limb in the central passageway.

The invention can be used to relieve pain associated with degenerative diseases and disorders by providing two intersecting donut shaped magnetic fields further intersecting a substantially planar field all within a central passageway of a frame and placing a biological subject in the intersecting magnetic field and exposing the biological subject to the magnetic field for a time period ranging from about 15 minutes up to several hours.

The method has been found useful for relieving pain associated with degenerative diseases and disorders categorized within the pain group consisting of: arthritis, limb, foot, and hand pain.

Each of the plurality of magnets embedded in a continuous side wall of a frame has a planar face with a north pole or south pole oriented towards the treatment area. All planar faces of the magnetic pairs have the same north or south pole magnetism.

The pairs of magnets are positioned to enable like poles to be adjacent one another.

All of the objects, features, and advantages of the present invention are believed to be within the scope of the present invention, even though they are not specifically set forth.

Data Example

The following example provides actual data obtained from 30 independent tests in humans to determine if the inventive device and method are useful for relieving pain associated with degenerative diseases and disorders. The summary of the data and results is set forth. The data illustrates a before and after pain rating for the various study participants. Some of the 30 participants indicated pain in more than one location of their body. Each participant completed the baseline (i.e., pre-treatment) tests, treatment, and follow-up phases of the study. The magnetic field exposure data and pain relief data was systematically collected, tabulated, and is set forth below in the tables. The apparatus and method of the present invention were found to be useful for relieving pain associated with degenerative diseases and disorders.

Turning now to the Figures, FIG. 1A is a cross sectional view of an embodiment of the present invention showing the relative orientation of the magnets in the sidewall of the frame. The apparatus is shown having the frame (20) and the continuous side wall (22) with and a central passageway (24). In an embodiment, the frame has an inner diameter ranging from about 2 inches to about 30 inches.

The continuous side wall can be a single formed material, such as by press molding or by forming from an extruder, and can be made from polyvinyl chloride, another non-deformable polymer, or a lightweight composite.

FIG. 1A further shows a liner (38), which can be optional and can be secured to the continuous side wall (22) on a side opposite the central passageway (24) for use in focusing the magnetic effect of the magnets into concentrated donut fields.

This liner can be made from a thick, non-metallic shielding material such as about ¼ inch to about ½ inch nonmagnetic material.

The frame as shown, is a substantially cylindrical frame, however, it can be rectangular or elliptical so long as when the magnets are embedded in the frame, two donut shaped magnetic fields are formed.

A bar (26) is disposed in the central passageway (24), extending from a first side of the continuous side wall (28) to a second side of the continuous side wall (30). The bar can be pivotably connected to the continuous side wall (22), allowing the bar (26) to swivel relative to the continuous side wall (22).

Four pairs of identical planar pole magnets (32a, 32b, 33a, 33b, 34a, 34b, 35a, and 35b) are embedded in the frame, and wherein each pair comprises two magnets which can have a planar face disposed adjacent the other and separated by less than about 1 inch and wherein the first pair is embedded opposite a second pair, and a third pair is embedded opposite a fourth pair, and the four pairs are oriented to form two intersecting donut shaped low gauss magnetic field. All magnets are represented with N and S to represent the north and south poles of the magnet.

The magnetic field can be contemplated to have a low gauss measurement between about 0 Tesla to about 2 Tesla.

A central magnet (36) nonremovably encircles the bar and can be disposed at the intersection of the donut shaped low gauss magnet field. The central magnet can be adapted for forming a substantially focused field. In FIG. 1A the bar (26) and the central magnet (36) are located approximately in the center so the bar and the central magnet can be grabbed by a hand.

Figure 1B:
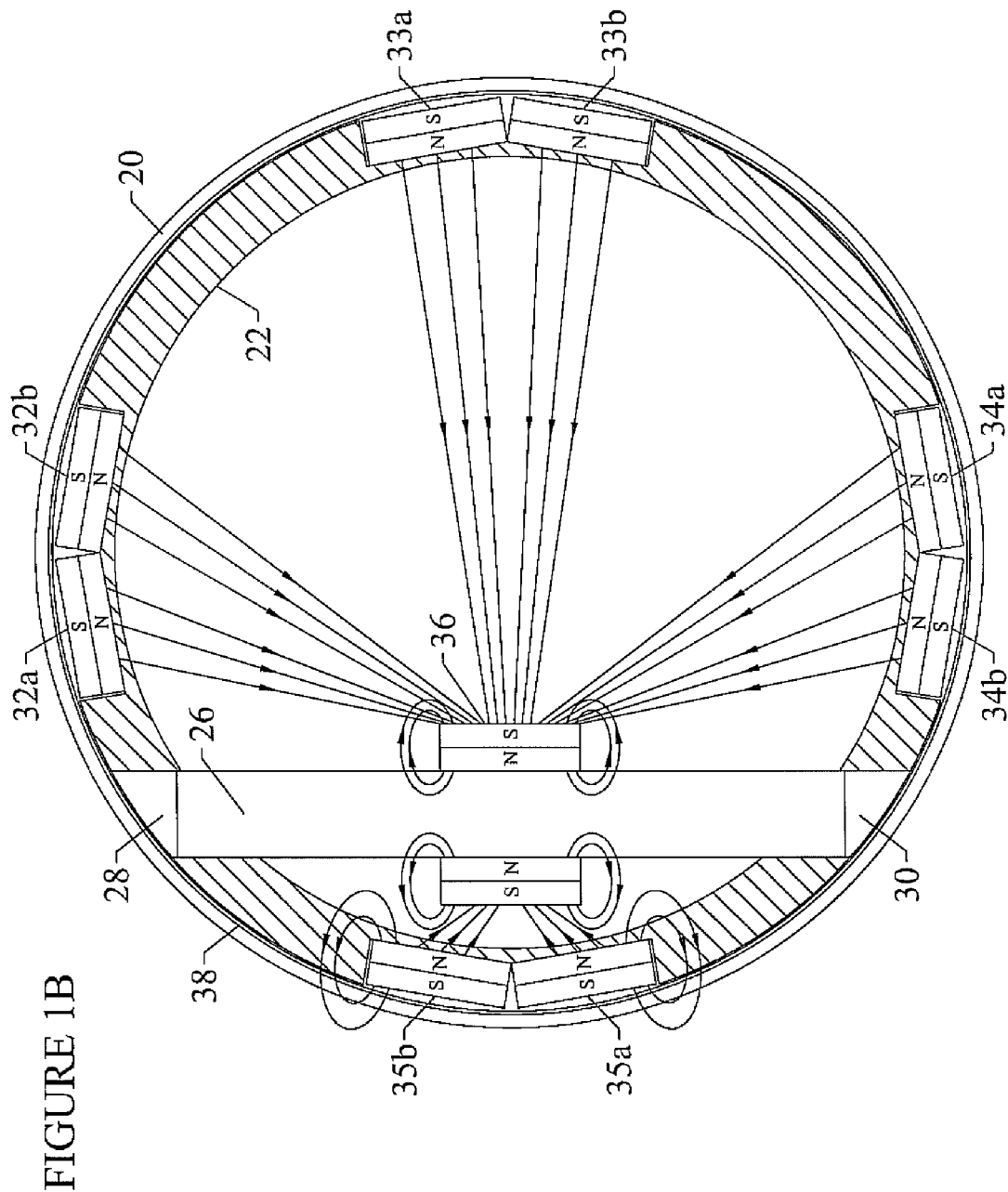
FIG. 1B is a cross-sectional view of an embodiment of the present invention showing the relative orientation of the magnets in the sidewall of the frame.

Turning now to FIG. 1B, the bar (26) is offset substantially to accommodate a foot on one side of the bar.

The configuration illustrated in FIG. 1A and FIG. 1B are examples of the present invention which can be practiced in a number or ways. Particularly, the magnet polarities can be arranged in a number of configurations so long as there is a focus around the central magnet. For example, the central magnet (36) can be orientated differently on each side of the bar.

Figure 2A:
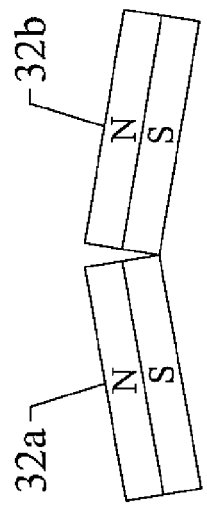
FIG. 2A is a side view of two of the four pairs of magnets shown in FIG. 1.
Figure 2B:
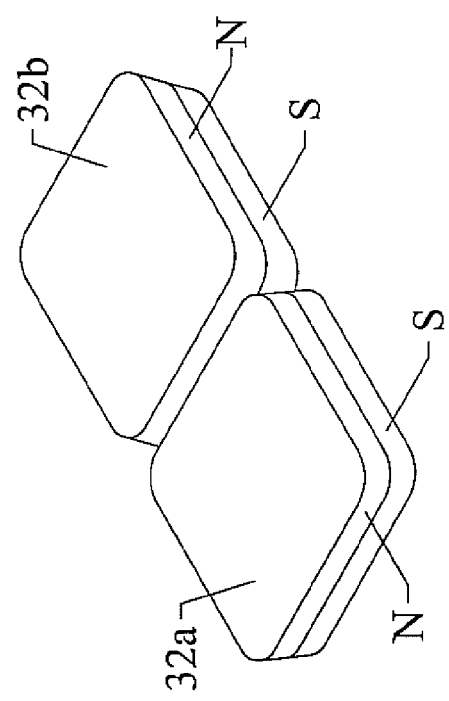
FIG. 2B is an isometric view of two of the four pairs of magnets shown in FIG. 1.
Figure 2C:
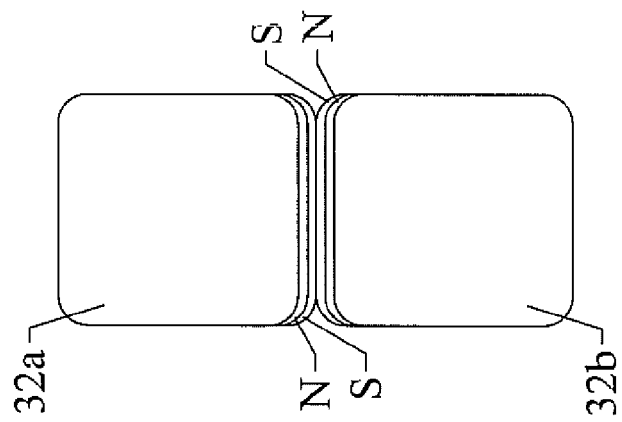
FIG. 2C is a top view of two of the four pairs of magnets shown in FIG. 1.

FIGS. 2A, 2B, and 2C illustrate two of the four pairs of magnets shown in FIG. 1A and FIG. 1B. A pair of identical planar pole magnets (32a, 32b) are shown with a width between about 0.5 inches to about 1.50 inches, a length between about 0.50 inches to about 1.50 inches and a thickness between about 0.10 inches to about 0.50 inches.

In an embodiment the magnets can be about 1 inch by about 1 inch squares with a thickness of about 0.25 inches. In an embodiment the poles can be on the flat square surfaces of the magnets. The magnets can be constructed from Neodymium Iron Boron (NdFeB). Each magnet is contemplated to generate between about 0 Tesla to about 2 Tesla. Each pair of magnets is contemplated to have the same polarity, shown in this Figure to be "north".

Figure 3:
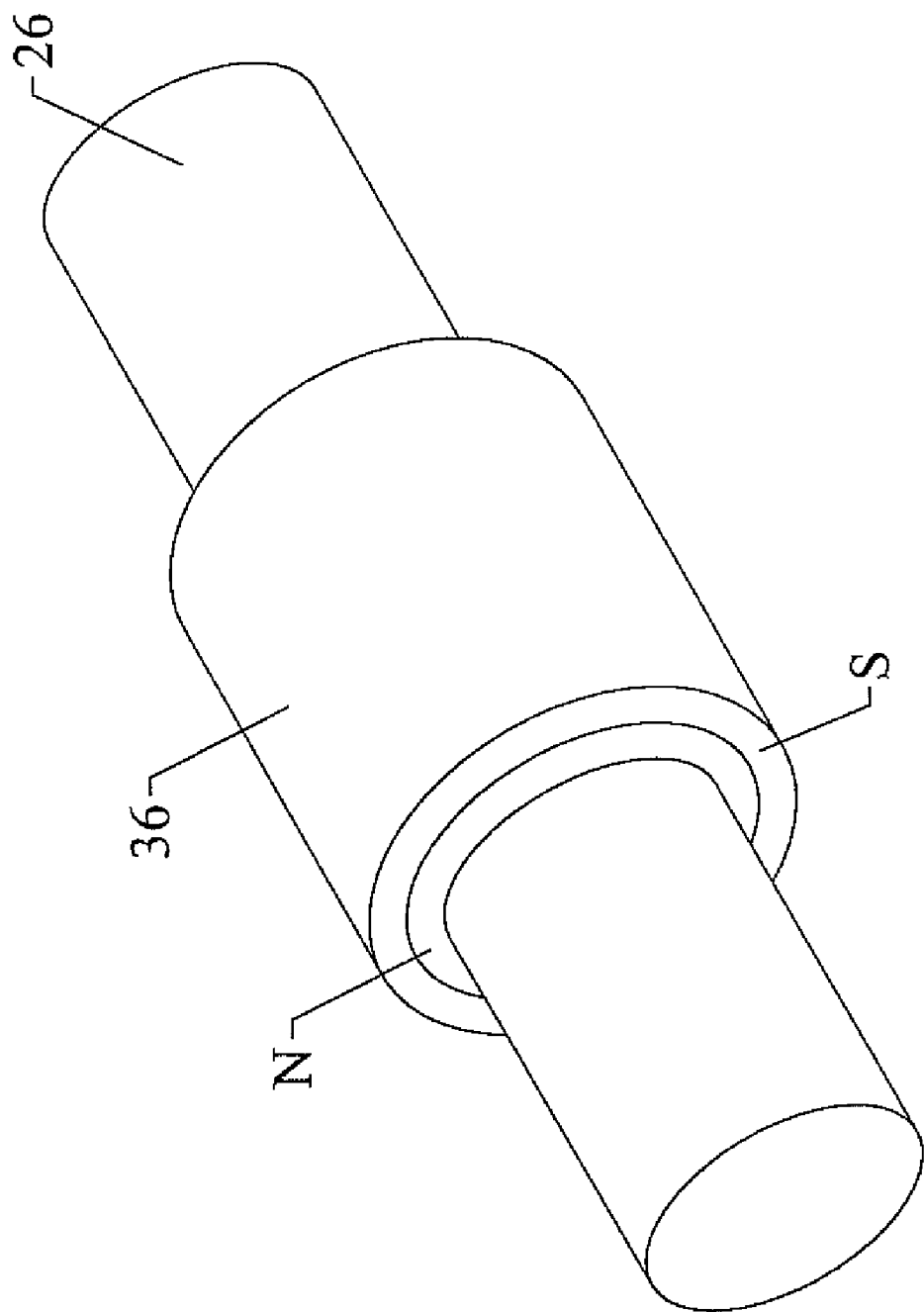
FIG. 3 shows a detail of the central magnet.

FIG. 3 shows a detail of the central magnet (36). The central magnet is contemplated to have a polarity opposite the polarity of the magnet pairs that are opposite the central magnet. The central magnet can have an outer diameter between about 1 inch to about 30 inches. The central magnet creates a focused field which can range in size from about 1 inch to about 30 inches.

While these embodiments have been described with emphasis on the embodiments, it should be understood that within the scope of the appended claims, the embodiments might be practiced other than as specifically described herein.

What is claimed is:

1. An apparatus for treating pain or chronic pain comprising:
   a. a frame with a continuous side wall and a central passageway extending there through;
   b. a bar disposed in the central passageway, extending from a first side of the continuous side wall to a second side of the continuous side wall;
   c. four pairs of identical planar pole magnets embedded in the frame, and wherein each pair of identical planar pole magnets comprises two magnets which can have a planar face disposed adjacent the other and separated by less than 1 inch and wherein the first pair can be embedded opposite a second pair, and a third pair can be embedded opposite a fourth pair, and the four pairs are oriented to form a low gauss magnetic field with two intersecting donut shapes; and
   d. a central magnet nonremovably encircling the bar and disposed at the intersection of the low gauss magnetic field with two intersecting donut shapes wherein a central magnet can be adapted for forming a substantially focused field, wherein the substantially focused field provides therapeutic relief of pain and swelling to an arm or leg placed on the bar disposed in the central passageway.

2. The apparatus of claim 1, further comprising a donut shaped low gauss field magnetic flux field between 0 Tesla to 2 Tesla.

3. The apparatus of claim 1, wherein the frame has an inner diameter ranging from 1 inch to 30 inches.

4. The apparatus of claim 1, wherein each magnet in the pairs of identical planar pole magnets have a width between 0.50 inches to 1.50 inches, a length between 0.50 inches to 1.50 inches, and a thickness between 0.10 inches to 0.50 inches.

5. The apparatus of claim 1, wherein each donut shaped low gauss magnetic field has a field diameter of no more than 30 inches.

6. The apparatus of claim 1, wherein the magnet pairs opposite to a central magnet have poles opposite the central magnet.

7. The apparatus of claim 1, wherein a central magnet has an outer diameter between 1 inch to 2 inches.

8. The apparatus of claim 1, wherein the apparatus can be used for relieving pain associated with degenerative diseases and disorders within the group consisting of: arthritis and limb pain.

9. The apparatus of claim 1, wherein the continuous side wall comprises polyvinyl chloride, a non-deformable polymer, or a lightweight composite.

10. The apparatus of claim 9, further comprising a liner disposed on the continuous side wall on a side opposite the embedded magnets to focus the magnetic effect of the magnets into concentrated donut fields.

11. The apparatus of claim 10, wherein the liner comprises a non-metallic shielding material.

12. The apparatus of claim 1, wherein the frame can be a substantially cylindrical frame.

* * * * *